(12) United States Patent
Mizuhara

(10) Patent No.: US 10,359,842 B2
(45) Date of Patent: Jul. 23, 2019

(54) INFORMATION PROCESSING SYSTEM AND INFORMATION PROCESSING METHOD

(71) Applicant: Takuya Mizuhara, Kanagawa (JP)

(72) Inventor: Takuya Mizuhara, Kanagawa (JP)

(73) Assignee: RICOH COMPANY, LIMITED, Tokyo (JP)

( * ) Notice: Subject to any disclaimer, the term of this patent is extended or adjusted under 35 U.S.C. 154(b) by 975 days.

(21) Appl. No.: 14/848,817

(22) Filed: Sep. 9, 2015

(65) Prior Publication Data
US 2016/0077585 A1    Mar. 17, 2016

(30) Foreign Application Priority Data

Sep. 16, 2014  (JP) .................. 2014-188295
Sep. 3, 2015   (JP) .................. 2015-174042

(51) Int. Cl.
*A61B 3/113*   (2006.01)
*A61B 5/00*    (2006.01)
*G06F 3/0482*  (2013.01)
*G06F 3/01*    (2006.01)
*G06F 3/0484*  (2013.01)
(Continued)

(52) U.S. Cl.
CPC .............. *G06F 3/013* (2013.01); *A61B 3/113* (2013.01); *A61B 5/00* (2013.01); *G06F 3/0482* (2013.01); *G06F 3/04842* (2013.01); *A61B 3/00* (2013.01); *G06K 9/00604* (2013.01)

(58) Field of Classification Search
None
See application file for complete search history.

(56) References Cited

U.S. PATENT DOCUMENTS 4,993,825 A * 2/1991 Abe ................. A61B 3/113
                                           351/206
5,886,768 A * 3/1999 Knopp ............. A61B 3/152
                                           351/212
(Continued)

FOREIGN PATENT DOCUMENTS

JP      11-224152       8/1999
JP      2000-010723     1/2000
(Continued)

*Primary Examiner* — Chanh D Nguyen
*Assistant Examiner* — Karin Kiyabu
(74) *Attorney, Agent, or Firm* — Harness, Dickey & Pierce, P.L.C.

(57) ABSTRACT

An information processing system includes: first and second information processing apparatuses; a detector that detects an eye-gaze direction of a user that uses the first information processing apparatus; a gaze point information generator that generates, on the basis of the eye-gaze direction, gaze point information indicating a position at which the user gazes on first screen information commonly displayed on the first and second information processing apparatuses; and a display controller that controls a display image to be displayed on the second information processing apparatus when calibration for determining a correspondence relation between the eye-gaze direction of the user and an actual gaze position is executed. The display image is generated on the first screen information and includes a second image displayed at a position indicated by the gaze point information and a third image displayed at a gaze instruction position at which the user is made to gaze.

19 Claims, 21 Drawing Sheets

(51) Int. Cl.
  *G06K 9/00* (2006.01)
  *A61B 3/00* (2006.01)

(56) References Cited

U.S. PATENT DOCUMENTS

| | | | | |
|---|---|---|---|---|
| 6,003,991 | A * | 12/1999 | Viirre | A61B 3/145 |
| | | | | 351/206 |
| 7,460,150 | B1 * | 12/2008 | Coughlan | H04N 7/147 |
| | | | | 348/14.01 |
| 9,462,226 | B1 * | 10/2016 | Mizuhara | G06F 3/013 |
| 9,619,023 | B2 * | 4/2017 | Mizuhara | G06F 19/3418 |
| 2009/0219484 | A1 * | 9/2009 | Ebisawa | A61B 3/113 |
| | | | | 351/210 |
| 2012/0092436 | A1 * | 4/2012 | Pahud | G06Q 10/10 |
| | | | | 348/14.02 |
| 2014/0168056 | A1 * | 6/2014 | Swaminathan | G06K 9/00604 |
| | | | | 345/156 |
| 2015/0199812 | A1 * | 7/2015 | Hakoshima | A61B 3/113 |
| | | | | 348/78 |
| 2015/0365658 | A1 * | 12/2015 | Devale | G06F 3/013 |
| | | | | 348/51 |
| 2016/0018888 | A1 * | 1/2016 | Buford | G06F 3/013 |
| | | | | 345/156 |
| 2016/0127427 | A1 * | 5/2016 | Bostick | H04L 65/403 |
| | | | | 709/205 |
| 2016/0210432 | A1 * | 7/2016 | Mizuhara | G06F 19/3418 |
| 2016/0234461 | A1 * | 8/2016 | Mizuhara | H04L 65/4023 |
| 2017/0344112 | A1 * | 11/2017 | Wilson | G06K 9/00 |
| 2018/0196511 | A1 * | 7/2018 | Chae | G06F 3/013 |

FOREIGN PATENT DOCUMENTS

| | | |
|---|---|---|
| JP | 2006-087751 | 4/2006 |
| JP | 2012-093895 | 5/2012 |

\* cited by examiner

FIG.6

| USER ID | NAME | SEX | AGE |
|---|---|---|---|
| 0001 | TARO YAMADA | MALE | 36 |

FIG.7

| USER ID | 0001 | | | |
|---|---|---|---|---|
| MEDICAL CHECKUP ITEM | 2014/05/01 | 2013/05/01 | 2012/05/01 | 2011/05/01 |
| HEIGHT | 170.5 | 170.4 | 170.6 | 170.8 |
| WEIGHT | 70.4 | 69.1 | 66.1 | 65.3 |
| BMI | 24.2 | 23.8 | 22.8 | 22.4 |
| BLOOD PRESSURE | 130 | 111 | 126 | 132 |
| URIC ACID | 6.4 | 6.5 | 6.8 | 6.1 |
| RED BLOOD CELL | 481 | 472 | 491 | 456 |
| NEUTRAL FAT | 172 | 178 | 173 | 167 |

FIG.8

| USER ID | 0001 |
|---|---|
| PAST MEDICAL HISTORY | ANSWER |
| HIGH-BLOOD PRESSURE | ○ |
| STROKE | × |
| CANCER | × |
| DIABETES | ○ |
| ARRHYTHMIA | × |
| BRONCHIAL ASTHMA | × |

FIG.9

| USER ID | 0001 |
|---|---|
| LIFESTYLE HABIT | ANSWER |
| SPORT HABIT | ONCE A WEEK |
| SMOKING | 10 OR MORE CIGARETTES A WEEK |
| DRINKING | 6 GO (ABOUT 1.06 LITTERS) A WEEK |
| SLEEPING HOURS | 6 HOURS ON AVERAGE |
| HAVE A LOT OF FRIED FOOD | ○ |
| CONSTIPATION | × |
| FEEL STRESSED | × |

FIG.12

GAZE POINT MARKER (SECOND IMAGE)

GAZE INSTRUCTION MARKER (THIRD IMAGE)

MEDICAL CHECKUP DATA

| DURING CALIBRATION NAME | SEX | AGE | | | |
|---|---|---|---|---|---|
| TARO YAMADA | MALE | | | | |

| MEDICAL CHECKUP ITEM | 2014/05/01 | 2013/05/01 | 2012/05/01 | 2011/05/01 |
|---|---|---|---|---|
| HEIGHT | 170.5 | 170.4 | 170.6 | 170.8 |
| WEIGHT | 70.4 | 69.1 | 66.1 | 65.3 |
| BMI | 24.2 | 23.8 | 22.8 | 22.4 |
| BLOOD PRESSURE | 130 | 111 | 126 | 132 |
| URIC ACID | 6.4 | 6.5 | 6.8 | 6.1 |
| RED BLOOD CELL | 481 | 472 | 491 | 456 |
| NEUTRAL FAT | 172 | 178 | 173 | 167 |

| PAST MEDICAL HISTORY | ANSWER |
|---|---|
| HIGH-BLOOD PRESSURE | ○ |
| STROKE | ● |
| CANCER | × |
| DIABETES | ○ |
| ARRHYTHMIA | × |
| BRONCHIAL ASTHMA | × |

| LIFESTYLE HABIT | ANSWER |
|---|---|
| SPORT HABIT | ONCE A WEEK |
| SMOKING | 10 OR MORE CIGARETTES A WEEK |
| DRINKING | 6 GO (ABOUT 1.06 LITTERS) A WEEK |
| SLEEPING HOURS | 6 HOURS ON AVERAGE |
| HAVE A LOT OF FRIED FOOD | ○ |
| CONSTIPATION | × |
| FEEL STRESSED | × |

FIG.13

MEDICAL CHECKUP DATA

| NAME | SEX | AGE |
|---|---|---|
| RO | MALE | 36 |

| MEDICAL CHECKUP ITEM | 2014/05/01 | 2013/05/01 | 2012/05/01 | 2011/05/01 |
|---|---|---|---|---|
| HEIGHT | 170.5 | 170.4 | 170.6 | 170.8 |
| WEIGHT | 70.4 | 69.1 | 66.1 | 65.3 |
| BMI | 24.2 | 23.8 | 22.8 | 22.4 |
| BLOOD PRESSURE | 130 | 111 | 126 | 132 |
| URIC ACID | 6.4 | 6.5 | 6.8 | 6.1 |
| RED BLOOD CELL | 481 | 472 | 491 | 456 |
| NEUTRAL FAT | 172 | 178 | 173 | 167 |

| PAST MEDICAL HISTORY | ANSWER |
|---|---|
| HIGH-BLOOD PRESSURE | ○ |
| STROKE | × |
| CANCER | × |
| DIABETES | ○ |
| ARRHYTHMIA | × |
| BRONCHIAL ASTHMA | × |

| LIFESTYLE HABIT | ANSWER |
|---|---|
| SPORT HABIT | ONCE A WEEK |
| SMOKING | 10 OR MORE CIGARETTES A WEEK |
| DRINKING | 6 GO (ABOUT 1.08 LITTERS) A WEEK |
| SLEEPING HOURS | 6 HOURS ON AVERAGE |
| HAVE A LOT OF FRIED FOOD | ○ |
| CONSTIPATION | × |
| FEEL STRESSED | × |

Labels: GAZE INSTRUCTION MARKER, GAZE POINT MARKER, DURING CALIBRATION

FIG.14

| | MEDICAL CHECKUP DATA | | | | |
|---|---|---|---|---|---|
| NAME | SEX | | AGE | | |
| RO | MALE | | 36 | | |
| MEDICAL CHECKUP ITEM | 2014/05/01 | 2013/05/01 | 2012/05/01 | 2011/05/01 | |
| HEIGHT | 170.5 | 170.4 | 170.6 | 170.8 | |
| WEIGHT | 70.4 | 69.1 | 66.1 | 65.3 | |
| BMI | 24.2 | 23.8 | 22.8 | 22.4 | |
| BLOOD PRESSURE | 130 | 111 | 126 | 132 | |
| URIC ACID | 6.4 | 6.5 | 6.8 | 6.1 | |
| RED BLOOD CELL | 481 | 472 | 491 | 456 | |
| NEUTRAL FAT | 172 | 178 | 173 | 167 | |

| PAST MEDICAL HISTORY | ANSWER |
|---|---|
| HIGH-BLOOD PRESSURE | O |
| STROKE | × |
| CANCER | × |
| DIABETES | O |
| ARRHYTHMIA | × |
| BRONCHIAL ASTHMA | × |

| LIFESTYLE HABIT | ANSWER |
|---|---|
| SPORT HABIT | ONCE A WEEK |
| SMOKING | 10 OR MORE CIGARETTES A WEEK |
| DRINKING | 6 GO (ABOUT 1.06 LITTERS) A WEEK |
| SLEEPING H | 6 HOURS ON AVERAGE |
| HAVE A LOT OF FRIED FOOD | O |
| CONSTIPATION | × |
| FEEL STRESSED | × |

DURING CALIBRATION

SELECTION RANGE

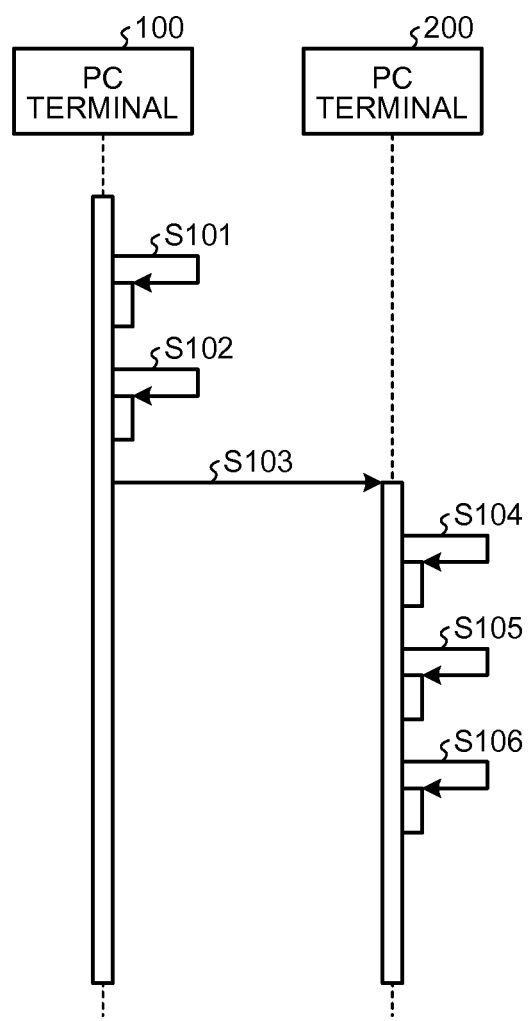

INFORMATION PROCESSING SYSTEM AND INFORMATION PROCESSING METHOD

CROSS-REFERENCE TO RELATED APPLICATIONS

The present application claims priority to and incorporates by reference the entire contents of Japanese Patent Application No. 2014-188295 filed in Japan on Sep. 16, 2014 and Japanese Patent Application No. 2015-174042 filed in Japan on Sep. 3, 2015.

BACKGROUND OF THE INVENTION

1. Field of the Invention

The present invention relates to an information processing system and an information processing method.

2. Description of the Related Art

Conventionally, there has been known a technique for detecting an eye-gaze direction of a user that gazes at a display screen of a computer using an eye-gaze sensor formed by an infrared light-emitting diode (LED) and an infrared camera. There are individual differences in the physical shape of eyeballs, thereby requiring calibration for determining a correspondence relation between an eye-gaze direction of a user and an actual gaze position.

For example, Japanese Patent Application Laid-open No. 2000-010723 discloses a calibration method that includes an initial calibration process for displaying a marker at a prescribed position on a display screen of a computer and performing calibration and a dynamic calibration process for re-executing calibration when an application is executed (whenever an event is generated).

When calibration is executed in the conventional technique, a gaze image (marker and the like) for making a subject gaze at is displayed on a display screen that the subject observes, and the calibration is advanced while the subject knows that the calibration is executed. However, there may be a case where a subject is not desired to be conscious of execution of calibration, for example, for the purpose of preventing psychological stress from being given to the subject.

SUMMARY OF THE INVENTION

It is an object of the present invention to at least partially solve the problems in the conventional technology.

An information processing system includes a first information processing apparatus and a second information processing apparatus communicable with the first information processing apparatus. The system further includes a detector, a gaze point information generator, and a display controller. The detector detects an eye-gaze direction of a first user that uses the first information processing apparatus. The gaze point information generator generates, on the basis of the eye-gaze direction, gaze point information indicating a position at which the first user gazes on first screen information commonly displayed on the first information processing apparatus and the second information processing apparatus. The display controller controls a display image to be displayed on the second information processing apparatus when calibration for determining a correspondence relation between the eye-gaze direction of the first user and an actual gaze position is executed. The display image is generated on the first screen information and includes a second image displayed at a position indicated by the gaze point information and a third image displayed at a gaze instruction position at which the first user is made to gaze.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 6 is a view illustrating an example of medical checkup data;

FIG. 7 is a view illustrating an example of the medical checkup data;

FIG. 8 is a view illustrating an example of the medical checkup data;

FIG. 9 is a view illustrating an example of the medical checkup data;

FIG. 12 is a view illustrating an example of a gaze point marker and a gaze instruction marker;

FIG. 13 is a view illustrating a method for determining a gaze instruction position in a first mode;

FIG. 14 is a view illustrating a method for determining a gaze instruction position in a second mode;

FIG. 15 is a sequence diagram illustrating an example of an operation procedure of the information processing system;

DETAILED DESCRIPTION OF THE PREFERRED EMBODIMENTS

An exemplary embodiment will be described below in greater detail with reference to the accompanying drawings.

Figure 1:
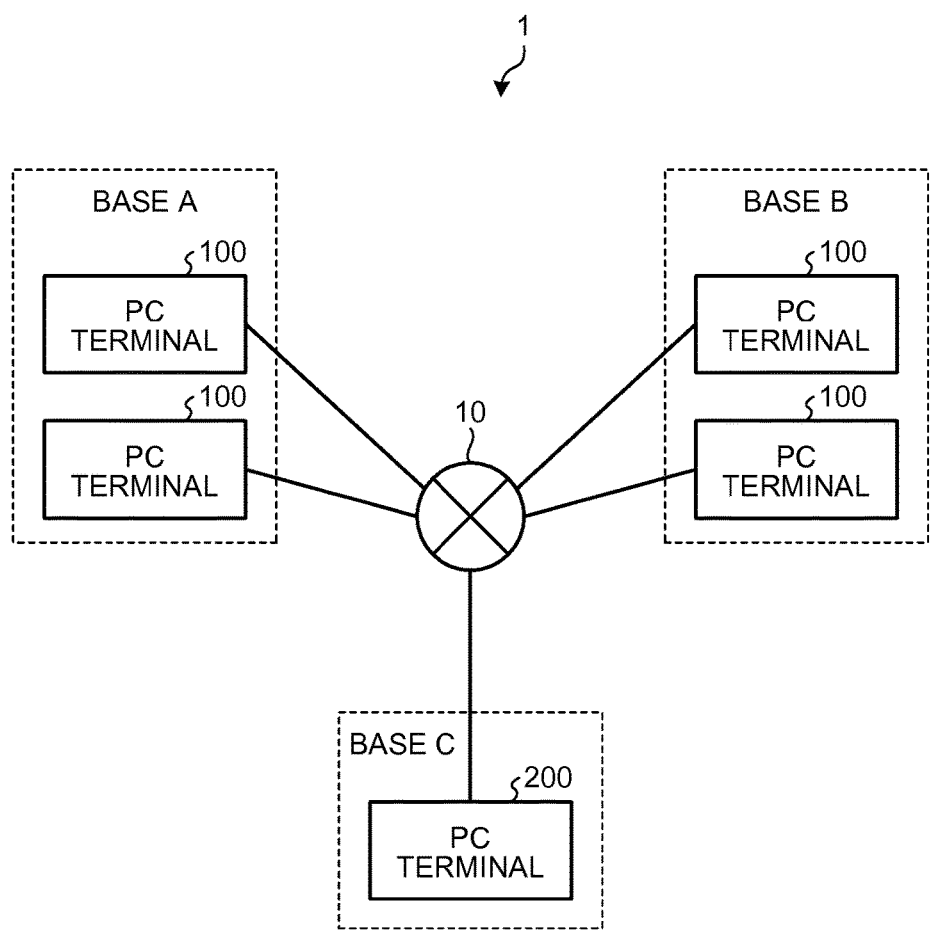
FIG. 1 is a view illustrating an example of the configuration of an information processing system according to an embodiment of the present invention.

FIG. 1 is a view illustrating an example of the configuration of an information processing system 1 according to the embodiment. In the example of FIG. 1, two personal computer (PC) terminals 100 are each disposed in a base A and a base B. In each of the base A and the base B, a subject (hereinafter may be referred to as "User A") exists. One personal computer (PC) terminal 200 is disposed in a base C where a doctor conducting a medical checkup and the like (hereinafter may be referred to as "User B") exists. The PC terminals 100 and the PC terminal 200 are connected to each other through a network 10 such as the Internet. As remote usage scenes of the information processing system 1 according to the embodiment, a relation where one is in a stronger position rather than both sides are in equal positions is assumed, for example, counseling between a doctor and a patient, mental healthcare between an industrial doctor and an employee, and an interview between a teacher and a student. A scene where a police officer investigates a criminal is also assumed. User A corresponds to a "first user" in claims and User B corresponds to a "second user" in claims.

Figure 2:
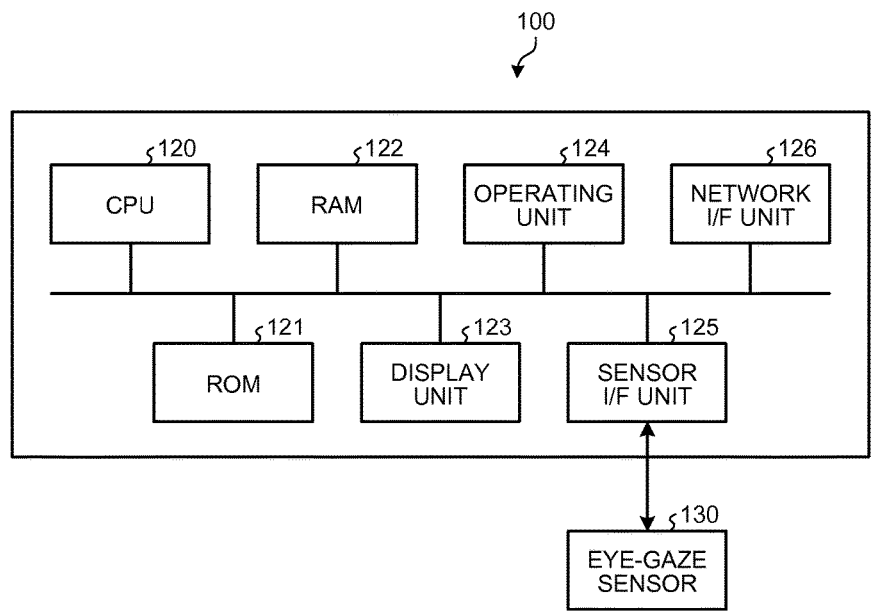
FIG. 2 is a view illustrating an example of the hardware configuration of a personal computer (PC) terminal that a subject uses.

FIG. 2 is a view illustrating an example of the hardware configuration of each PC terminal 100 that User A uses. As illustrated in FIG. 2, the PC terminal 100 includes a central processing unit (CPU) 120, read only memory (ROM) 121, random access memory (RAM) 122, a display unit 123, an operating unit 124, a sensor interface (I/F) unit 125, and a network I/F unit 126. The CPU 120 integrally controls operation of the PC terminal 100. The ROM 121 is nonvolatile memory that stores therein various kinds of data such as a computer program. The RAM 122 is volatile memory that functions as a work area (task area) of the CPU 120. The display unit 123 is a device that displays various kinds of information, and may be formed by, for example, a liquid crystal display. The operating unit 124 is a device used for various kinds of operation, and may be formed by, for example, a keyboard, a mouse and the like. The sensor I/F unit 125 is an interface for connecting with an eye-gaze sensor 130 formed by an infrared light-emitting diode (LED) and an infrared camera. The network I/F unit 126 is an interface for connecting with the network 10.

Figure 3:
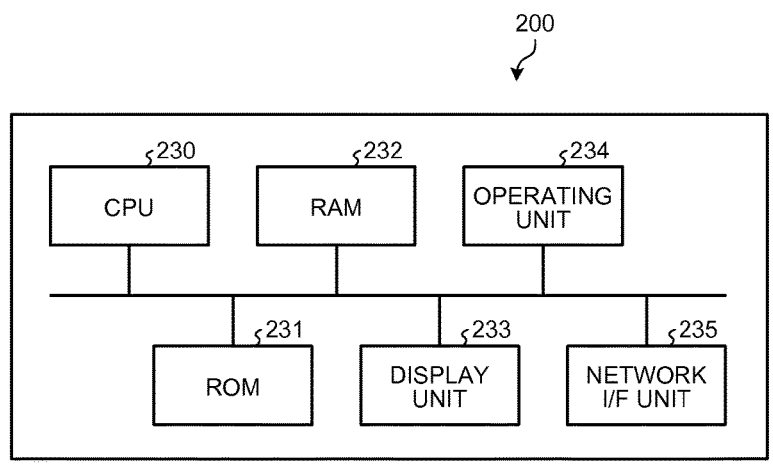
FIG. 3 is a view illustrating an example of the hardware configuration of a personal computer (PC) terminal that a doctor uses.

FIG. 3 is a view illustrating an example of the hardware configuration of the PC terminal 200 that User B uses. As illustrated in FIG. 3, the PC terminal 200 includes a central processing unit (CPU) 230, read only memory (ROM) 231, random access memory (RAM) 232, a display unit 233, an operating unit 234, and a network I/F unit 235. The CPU 230 integrally controls operation of the PC terminal 200. The ROM 231 is nonvolatile memory that stores therein various kinds of data such as a computer program. The RAM 232 is volatile memory that functions as a work area (task area) of the CPU 230. The display unit 233 is a device that displays various kinds of information, and may be formed by, for example, a liquid crystal display. The operating unit 234 is a device used for various kinds of operation, and may be formed by, for example, a keyboard, a mouse and the like. The network I/F unit 235 is an interface for connecting with the network 10.

Figure 4:
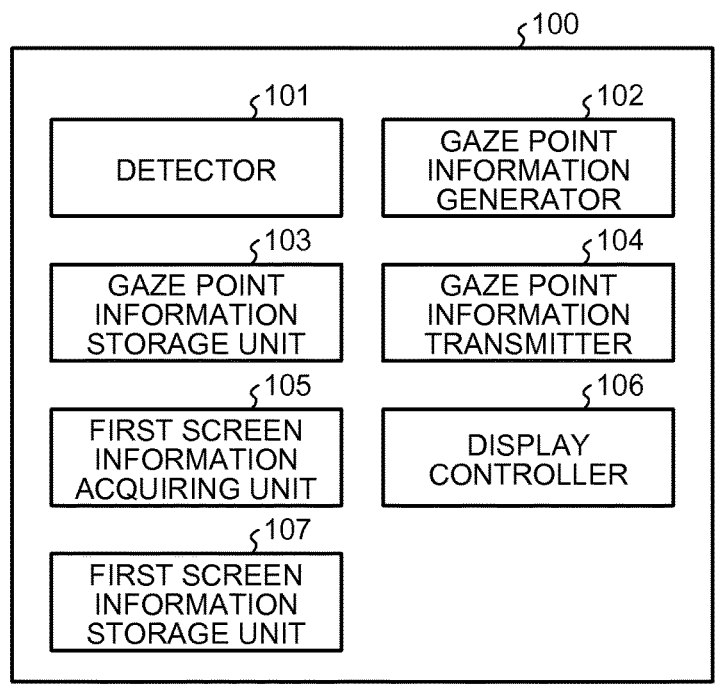
FIG. 4 is a view illustrating an example of the functional configuration of the PC terminal that the subject uses.

FIG. 4 is a view illustrating an example of the functional configuration of the PC terminal 100. As illustrated in FIG. 4, each PC terminal 100 includes a detector 101, a gaze point information generator 102, a gaze point information storage unit 103, a gaze point information transmitter 104, a first screen information acquiring unit 105, a display controller 106, and a first screen information storage unit 107. The example of FIG. 4 mainly exemplifies functions according to the present invention for convenience of explanation, but functions that the PC terminal 100 has are not limited to these functions.

Figure 5:
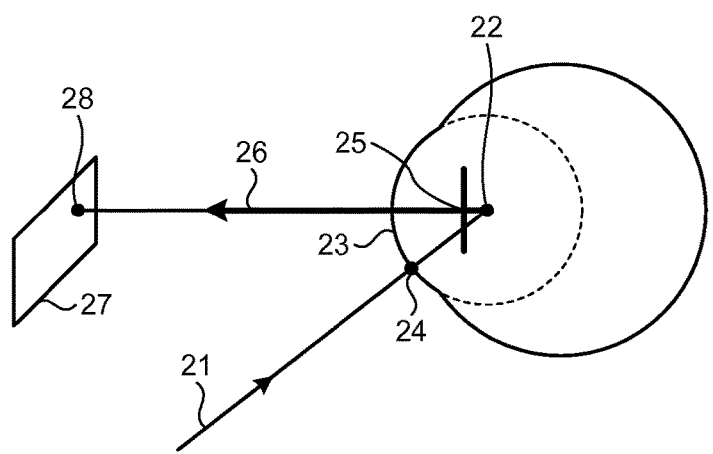
FIG. 5 is a view illustrating a method for detecting an eye-gaze direction.

The detector 101 uses a detection result from the eye-gaze sensor 130 to detect an eye-gaze direction of User A. The gaze point information generator 102 generates gaze point information that indicates a position at which User A gazes in first screen information displayed on the PC terminal 100 (display unit 123), on the basis of the eye-gaze direction detected by the detector 101. Known methods, for example, a corneal reflection method disclosed in Japanese Patent Application Laid-open No. 2006-87751 can be used as a method for detecting an eye-gaze direction. FIG. 5 is a view illustrating a corneal reflection method. As illustrated in FIG. 5, when infrared rays 21 enter a corneal curvature center 22 of an eye, corneal reflection (Purkinje image) 24 can be made on a cornea 23. An eye-gaze direction 26 from a pupil center 25 is directed to an upper right point 28 on a screen 27. The corneal reflection method is a method for detecting the corneal reflection (Purkinje image) 24 of the infrared rays 21 to be moved in parallel along with eyeball movement due to the difference in the rotation center of the cornea 23 and the eyeball. Specifically, a face of User A is irradiated with an infrared LED, and eyes of User A are imaged by an infrared camera. The position (corneal reflection 24) of reflected light formed by irradiation of the infrared LED on the cornea 23 is defined as a reference point. The eye-gaze direction 26 is detected on the basis of a position of a pupil with respect to the position of the corneal reflection 24. For example, if a pupil is on the outer corner side of a left eye rather than the corneal reflection 24 of the left eye, it can be detected that User A looks at a left side direction, and if a pupil is on the inner corner side of a left eye rather than the corneal reflection 24 of the left eye, it can be detected that User A looks at a right side direction.

The first screen information is screen information commonly displayed on the PC terminals 100 and the PC terminal 200. The screen information is information on a display target and is not limited to images. In this example, the first screen information is medical checkup data that indicates a result of a medical checkup of User A, but the first screen information is not limited to this. A data format of medical checkup data is arbitrary, and may be, for example, table-format data. FIGS. 6 to 9 are views illustrating examples of medical checkup data. FIG. 6 is table-format data where a user ID "0001" is associated with a name, sex, and age. FIG. 7 is table-format data where the user ID "0001" is associated with a date (medical checkup data) and a result of medical checkup items. FIG. 8 is table-format data where the user ID "0001" is associated with a past medical history. FIG. 9 is table-format data where the user ID "0001" is associated with a result of a lifestyle habit.

The gaze point information storage unit 103 stores therein gaze point information. Whenever gaze point information is generated by the gaze point information generator 102, the gaze point information transmitter 104 transmits the gaze point information (the latest gaze point information stored in the gaze point information storage unit 103) to the PC terminal 200.

The first screen information acquiring unit 105 acquires first screen information distributed from the PC terminal 200. The display controller 106 controls various kinds of information to be displayed on the display unit 123. For example, the display controller 106 controls the first screen information acquired by the first screen information acquiring unit 105 to be displayed on the display unit 123.

The first screen information storage unit 107 stores therein the first screen information acquired by the first screen information acquiring unit 105. For example, when medical checkup data as the first screen information is table-format data, the first screen information storage unit 107 stores values in a preliminarily prepared table so as to store therein the medical checkup data.

In this example, the CPU 120 in the PC terminal 100 executes a computer program stored in the ROM 121 and the like so as to achieve functions of the gaze point information generator 102, the gaze point information transmitter 104, the first screen information acquiring unit 105, and the display controller 106, but this is not limiting. For example, a dedicated hardware circuit (semiconductor integrated circuit and the like) may achieve at least a part of these functions.

Figure 10:
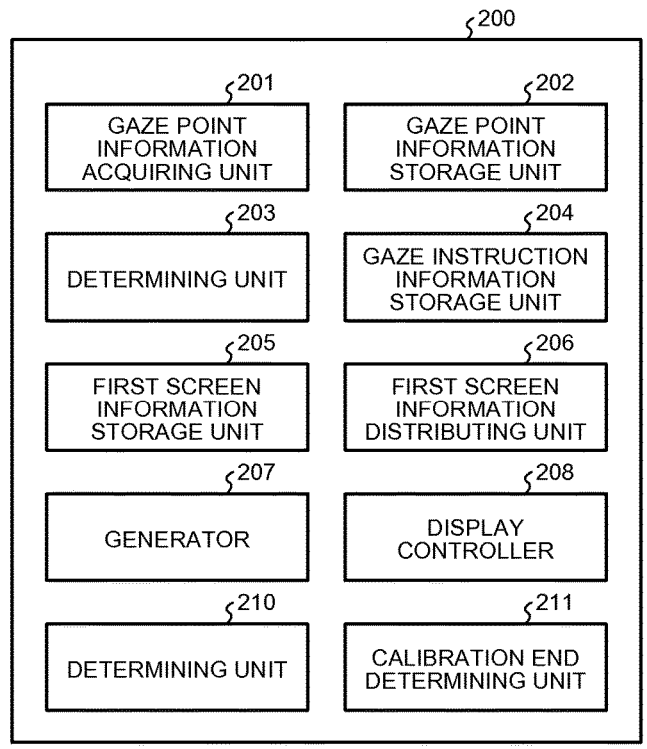
FIG. 10 is a view illustrating an example of the functional configuration of the PC terminal that the doctor uses.

FIG. 10 is a view illustrating an example of the functional configuration of the PC terminal 200. As illustrated in FIG. 10, the PC terminal 200 includes a gaze point information acquiring unit 201, a gaze point information storage unit 202, a determining unit 203, a gaze instruction information storage unit 204, a first screen information storage unit 205, a first screen information distributing unit 206, a generator 207, a display controller 208, a determining unit 210, and a calibration end determining unit 211. The example of FIG. 10 mainly exemplifies functions according to the present invention for convenience of explanation, but functions that the PC terminal 200 has are not limited to these functions.

The gaze point information acquiring unit 201 acquires gaze point information from each of the PC terminals 100. The gaze point information storage unit 202 stores therein the gaze point information acquired by the gaze point information acquiring unit 201.

The determining unit 203 determines a gaze instruction position at which User B is made to gaze in the first screen information commonly displayed on the PC terminals 100 and the PC terminal 200 with reception of a start instruction of calibration as a trigger, and generates gaze instruction information indicating the determined gaze instruction position. In this example, modes (methods) for determining a gaze instruction position include a mode for automatically determining a gaze instruction position (hereinafter may be referred to as a "first mode") and a mode for manually determining a gaze instruction position (hereinafter may be referred to as a "second mode"), and User B can select any one of the modes. The modes described above are not limiting, and, for example, any one of the first and second modes may be preliminary determined to be a mode for determining a gaze instruction position. Specific contents of a method for determining a gaze instruction position will be described later.

The gaze instruction information storage unit 204 stores therein gaze instruction information generated by the determining unit 203. The first screen information storage unit 205 stores therein first screen information. Similarly to the first screen information storage unit 107 in the PC terminal 100, for example, when medical checkup data as the first screen information is table-format data, the first screen information storage unit 205 stores values in a preliminarily prepared table so as to store therein the medical checkup data. The first screen information distributing unit 206 distributes the first screen information stored in the first screen information storage unit 205 to the PC terminals 100.

The generator 207 generates, on the first screen information, a display image including a second image displayed at a position indicated by gaze point information and a third image displayed at a gaze instruction position. Hereinafter, the first screen information may be referred to as "medical checkup data", the second image as a "gaze point marker", and the third image as a "gaze instruction marker". In this example, whenever the gaze point information acquiring unit 201 acquires new gaze point information or whenever the determining unit 203 determines a new gaze instruction position during execution of calibration, the generator 207 generates a display image on the basis of the latest gaze point information and gaze instruction information, and the display controller 208, which will be described later, controls the generated display image to be displayed on the display unit 233. In other words, when calibration for determining a correspondence relation between an eye-gaze direction of User A and an actual gaze position is executed, the display controller 208 controls the display image including the second image displayed at a position indicated by the gaze point information and the third image displayed at a gaze instruction position at which User A is made to gaze on the first screen information to be displayed on the display unit 233.

The display controller 208 controls various kinds of information to be displayed on the display unit 233. For example, the display controller 208 controls a display image generated by the generator 207 to be displayed on the display unit 233.

The determining unit 210 determines whether User A gazes at a gaze instruction position (determines whether a gaze instruction is ended). Specific contents thereof will be described later. The calibration end determining unit 211 determines whether calibration is ended. Specific contents thereof will be described later.

In this example, the CPU 230 in the PC terminal 200 executes a computer program stored in the ROM 231 and the like so as to achieve functions of the gaze point information acquiring unit 201, the determining unit 203, the first screen information distributing unit 206, the generator 207, the display controller 208, the determining unit 210, and the calibration end determining unit 211, but this is not limiting. For example, a dedicated hardware circuit (semiconductor integrated circuit and the like) may achieve at least a part of these functions.

Figure 11:
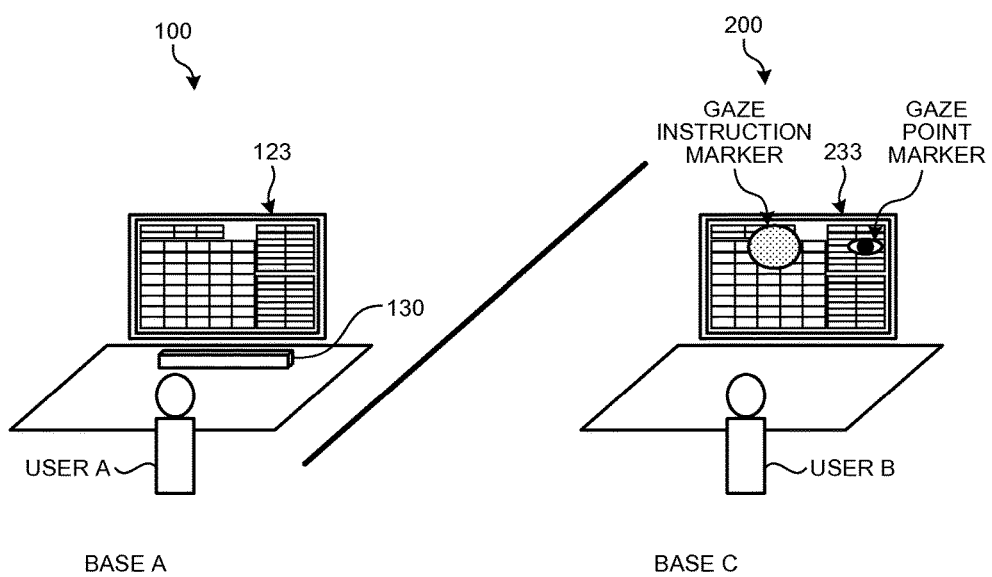
FIG. 11 is a schematic view illustrating the information processing system according to the embodiment.

As illustrated in FIG. 11, the following describes more specific contents with one PC terminal 100 that User A in the base A uses (which corresponds to a "first information processing apparatus" in claims) and the PC terminal 200 that User B in the base C uses (which corresponds to a "second information processing apparatus" in claims) as an example. The example of FIG. 11 illustrates that the eye-gaze sensor 130 is disposed beneath the display unit 123 on which the first screen information is displayed. The eye-gaze sensor 130 is typically formed by an infrared LED and an infrared camera. However, this is not limiting, and known and various kinds of configurations may be employed. For example, a visible light camera may be used. The PC terminal 100 uses a detection result from the eye-gaze sensor 130 to generate gaze point information indicating a position at which User A gazes in the first screen information displayed on the PC terminal 100 (display unit 123). There are individual differences in the shape of eyeballs, thereby requiring calibration for determining a correspondence relation between an eye-gaze direction of User A and an actual gaze position.

The PC terminal 200 causes a display image that includes a gaze point marker and a gaze instruction marker on the first screen information commonly displayed on the PC terminal 200 and the PC terminal 100 to be displayed on the display unit 233. User B sees a gaze instruction marker displayed on the display unit 233, and instructs User A to gaze at an item displayed at the position (any item out of a plurality of items included in medical checkup data) so as to perform calibration.

FIG. 12 illustrates an example of the gaze point marker and the gaze instruction marker. In the example of FIG. 12, a position corresponding to the gaze point information acquired from the PC terminal 100 in the medical checkup data displayed on the PC terminal 200 indicates a position of an answer item to a question whether a "stroke" falls under a past medical history in a plurality of items in the medical checkup data. In other words, it is indicated that User A in the base A gazes at, out of a plurality of items included in the medical checkup data displayed on the PC terminals 100, an answer item to a question whether a "stroke" falls under a past medical history, and the gaze point marker is displayed at a position of an answer item to a question whether a "stroke" falls under a past medical history in the medical checkup data displayed on the PC terminal 200.

In the example of FIG. 12, a gaze instruction position indicated by the gaze instruction information indicates a position of an "age" item of a user named "Taro Yamada" out of a plurality of items included in the medical checkup data, and a gaze instruction marker is displayed at a position of an "age" item of a user named "Taro Yamada" out of the medical checkup data displayed on the PC terminal 200. In the example of FIG. 12, when calibration starts, a display image including a gaze point marker, a gaze instruction marker, and a character string of "during calibration" on the medical checkup data (in this example, a display image formed by superimposing (combining) a gaze point marker, a gaze instruction marker, and a character string of "during calibration" on the medical checkup data) is displayed on the PC terminal 200 (display unit 233).

The following describes an example of a method for determining a gaze instruction position. The first screen information commonly displayed on the PC terminals 100 and the PC terminal 200 includes a plurality of characteristic areas capable of being gazed at by User A in the base A. For example, each of the characteristic areas may be an area corresponding to one item out of a plurality of items included in a table structure. As described above, the first screen information is medical checkup data in this example and each of the items included in the medical checkup data corresponds to each of the characteristic areas, but this is not limiting.

The following describes an example of a method for determining a gaze instruction position in the first mode (mode for automatically determining a gaze instruction position). In this case, the determining unit 203 in the PC terminal 200 automatically determines any one of the characteristic areas (in this example, any one of the items included in the medical checkup data) to be a gaze instruction position according to a predetermined rule. When the determining unit 210 determines that User A gazes at a gaze instruction position, the determining unit 203 determines a characteristic area different from a characteristic area corresponding to the gaze instruction position that is determined to have been gazed at by User A, to be a new gaze instruction position. As described above, in the embodiment, whenever the determining unit 203 determines a new gaze instruction position (or whenever the gaze point information acquiring unit 201 acquires new gaze point information) during execution of calibration, the generator 207 regenerates a display image including a gaze point marker, a gaze instruction marker, and a character string of "during calibration" on the medical checkup data on the basis of the latest gaze point information and gaze instruction information, and the display controller 208 controls the generated display image to be displayed on the display unit 233. This series of processing is repeated until calibration is ended. The following describes specific contents of a method for determining a gaze instruction position with reference to FIG. 13.

In the example of FIG. 13, medical checkup data includes a first table structure 11 representing basic information on a user including items of a name, sex, and age, a second table structure 12 representing medical checkup items such as height and weight and medical checkup dates, a third table structure 13 representing questions and answers related to a past medical history, and a fourth table structure 14 representing questions and answers related to a lifestyle habit. In the example of FIG. 13, the determining unit 203 sequentially determines the central item in the left end of each table structure as a gaze instruction position in the order of the first table structure 11, the second table structure 12, the third table structure 13, and the fourth table structure 14. In the example of FIG. 13, numerals (1 to 4) attached to gaze instruction markers represent the order of determining an item as the gaze instruction position.

When selecting the central item in the left end of the table structure, if a table structure is formed by a plurality of rows and the number of rows is even, a row where a value obtained by dividing the number of rows by two is assigned as a row numeral is selected. If a table structure is formed by a plurality of rows and the number of rows is odd, a row where a value obtained by adding only one to the number of rows and dividing the number of rows by two is assigned as a row numeral is selected. As an example, in the second table structure 12 illustrated in FIG. 13, the number of rows is eight, "four" obtained by dividing eight by two is assigned to the fourth row "BMI" as a row numeral, and the fourth row "BMI" is selected out of the examination items in the left end. In the third table structure 13, the number of rows is seven, "four" obtained by adding only one to seven and dividing eight by two is assigned to the fourth row "cancer" as a row numeral, and the fourth row "cancer" is selected out of the items of a past medical history in the left end.

Whenever the determining unit 210 determines that User A gazes at a gaze instruction position, the determining unit 203 determines a next item in the order as a new gaze instruction position, and repeats the above-mentioned determining processing until the determining unit 203 determines all the items of a predetermined number (in the example of FIG. 13, a predetermined number is four, but the predetermined number is not limited to this). In the example of FIG. 13, the central item in the left end of each table structure is sequentially determined as a gaze instruction position in the order of the first table structure 11, the second table structure 12, the third table structure 13, and the fourth table structure 14, but this is not limiting. The kinds and the number of items, and the determining order of a gaze instruction position can be arbitrarily defined.

For example, when User A is not determined to gaze at a gaze instruction position within a certain period time after the gaze instruction position is determined, the determining unit 203 may skip an item corresponding to the gaze instruction position and determine a next item in the order as a new gaze instruction position. For example, after User A is determined to gaze at a gaze instruction position corresponding to an item other than the skipped item, the determining unit 203 may determine an item near the skipped item as a new gaze instruction position. In short, when User A is not determined to gaze at a gaze instruction position within a certain period time after the gaze instruction position is determined, the determining unit 203 may determine an item different from an item corresponding to the gaze instruction position as a new gaze instruction position.

The following describes an example of a method for determining whether User A gazes at a gaze instruction position. In the embodiment, the determining unit 210 determines whether User A in the base A gazes at a gaze instruction position on the basis of a position relation between a gaze point marker (second image) and a gaze instruction marker (third image). More specifically, when the area of a superimposition region indicating a region formed by superimposing a gaze point marker and a gaze instruction marker is equal to or greater than a threshold, the determining unit 210 determines that User A gazes at a gaze instruction position. The threshold is arbitrarily changeable. For example, a value corresponding to 50% of the size of any one of the gaze point marker and the gaze instruction marker (for example, the one smaller in size) can be defined as the threshold, and a value corresponding to 100% can be defined as the threshold.

However, this is not limiting. For example, the determining unit 210 may determine whether the superimposition region is equal to or greater than a threshold in a predetermined cycle (for example, a one second cycle), and determine, if the number of times when the superimposition region is determined to be equal to or greater than a threshold in a certain period is equal to or greater than a certain number (for example, three times in five seconds), that User A gazes at a gaze instruction position.

For example, when an item corresponding to gaze point information (item where a gaze point marker is displayed) is identical to an item corresponding to gaze instruction information (item where a gaze instruction marker is displayed) out of a plurality of items included in the medical checkup data (one example of the characteristic areas), the determining unit 210 may determine that User A gazes at a gaze instruction position. Similarly to the above-mentioned case, for example, the determining unit 210 may determine whether an item corresponding to gaze point information is identical to an item corresponding to gaze instruction information in a predetermined cycle (for example, a one second cycle), and determine, if the number of times when they are determined to be identical in a certain period is equal to or greater than a certain number (for example, three times in five seconds), that User A gazes at a gaze instruction position.

The following describes an example of a method for determining whether calibration is ended. In the embodiment, with respect to a plurality of items preliminary set to be determined as gaze instruction positions according to the above-mentioned rule, when User A is determined to gaze at a gaze instruction position corresponding to each of the items, the calibration end determining unit 211 in the PC terminal 200 determines that calibration is ended.

The following describes an example of a method for determining a gaze instruction position in the second mode (mode for manually determining a gaze instruction position). In this case, the determining unit 203 determines any one of the items as a gaze instruction position in accordance with the selection instruction by User B. For example, the determining unit 203 can divide the medical checkup data into a plurality of selection ranges each including one or more items and determine at least one of the selection ranges out of the selection ranges as a selection range capable of receiving the selection instruction by User B. The following describes specific contents of a method for determining a gaze instruction position with reference to FIG. 14.

In the example of FIG. 14, the determining unit 203 determines, out of six selection ranges formed by dividing the medical checkup data into six equal parts, at least one of the selection ranges as a selection range capable of receiving a selection instruction by User B, and determines any item included in the selection range as a gaze instruction position in accordance with the selection instruction by User B. The number of selection ranges is not limited to six, and the size of a plurality of selection ranges is individually changeable. For example, a plurality of selection ranges may have different size. In the example of FIG. 14, whenever the determining unit 210 determines that User A gazes at a gaze instruction position, the determining unit 203 determines any one selection range out of six selection ranges as a selection range capable of receiving a selection instruction by User B according to a predetermined order, and waits for the selection instruction by User B so as to determine a new gaze instruction position. The determination method by the determining unit 210 is the same as that of the first mode. In the example of FIG. 14, numerals (1 to 6) attached to gaze point markers represent the order of determining a selection range including the gaze point marker as a selection range capable of receiving a selection instruction by User B, but this order is an example and is arbitrarily changeable.

Similarly to the first mode, whenever the determining unit 203 determines a new gaze instruction position (or whenever the gaze point information acquiring unit 201 acquires new gaze point information) during execution of calibration, the generator 207 regenerates a display image including a gaze point marker, a gaze instruction marker, and a character string of "during calibration" on the medical checkup data on the basis of the latest gaze point information and gaze instruction information, and the display controller 208 controls the generated display image to be displayed on the display unit 233. This series of processing is repeated until calibration is ended.

In the example of FIG. 14, when User A in the base A is determined to gaze at a gaze instruction position determined in accordance with the selection instruction by User B in each of the six selection ranges, the calibration end determining unit 211 determines that calibration is ended, but a method for determining the end is not limited to this. For example, in a mode where no selection range is defined and User B can select an arbitrary item in the medical checkup data as a gaze instruction position, when User A is determined to gaze at a gaze instruction position corresponding to each of the items present in the position required for calibration, the calibration end determining unit 211 may determine that calibration is ended. In this mode, the determining unit 203 can control User B to be notified of information for urging a selection instruction of an item corresponding to a position necessary for calibration out of the medical checkup data. The form of notification is arbitrary, for example, voice may be output, and an image and a text may be displayed on the display unit 233.

In short, with respect to each of a plurality of characteristic areas necessary for calibration (in this example, items included in the medical checkup data), when User A in the base A is determined to gaze at a gaze instruction position corresponding to each of the characteristic areas, the calibration end determining unit 211 may determine that the calibration is ended.

FIG. 15 is a sequence diagram illustrating an example of an operation procedure of the information processing system 1 according to the embodiment. It is assumed that medical checkup data serving as the first screen information is displayed on the PC terminal 100 (display unit 123) in the base A and the PC terminal 200 (display unit 233) in the base C.

User A in the base A gazes at the PC terminal 100 (display unit 123), and the PC terminal 100 (detector 101) detects an eye-gaze direction of User A (Step S101). The gaze point information generator 102 in the PC terminal 100 generates the gaze point information on the basis of the eye-gaze direction of User A as described above (Step S102).

The PC terminal 100 (gaze point information transmitter 104) transmits the gaze point information generated at Step S102 to the PC terminal 200 (Step S103). The PC terminal 200 (generator 207, display controller 208) displays, on the display unit 233, a display image (in this example, a display image formed by superimposing (combining) a gaze point marker on the medical checkup data) including, on medical checkup data displayed on the display unit 233, a gaze point marker that is displayed at a position corresponding to the gaze point information transmitted at Step S103 out of the medical checkup data (Step S104).

User B in the base C can check which position User A in the base A gazes at in the medical checkup data by checking a gaze point marker displayed on the PC terminal 200 (display unit 233). A flow from Step S101 to Step S104 is repeatedly executed until the PC terminal 100 and the PC terminal 200 are disconnected regardless of whether calibration is executed.

User B inputs an instruction for starting calibration to the PC terminal 200 and inputs an instruction for selecting any one of the first mode and the second mode, and the PC terminal 200 (determining unit 203) determines any one of the first mode and the second mode as a mode for determining a gaze instruction position (Step S105). The PC terminal 200 (determining unit 203) determines the gaze instruction position on the basis of the determined mode.

The PC terminal 200 (generator 207, display controller 208) displays, on the display unit 233, a display image including, on medical checkup data displayed on the PC terminal 200, a gaze point marker displayed at a position corresponding to the latest gaze point information in the medical checkup data and a gaze instruction marker displayed at a gaze instruction position in the medical checkup data (Step S106).

User B can check which item User A is made to gaze at in the medical checkup data by checking a gaze instruction marker displayed on the PC terminal 200 (display unit 233), and instructs User A to gaze at an item corresponding to the gaze instruction marker. The form of this instruction is arbitrary, and, for example, the PC terminals 100 may output information indicating an item to be gazed at in the medical checkup data using communication between the PC terminal 100 and the PC terminal 200 (may output voice and may display image information and a text on the display unit 233), and, for example, a speech function of a phone and the like may be used to give an instruction. A flow from Step S105 to Step S106 is repeatedly executed until calibration is ended.

Figure 16:
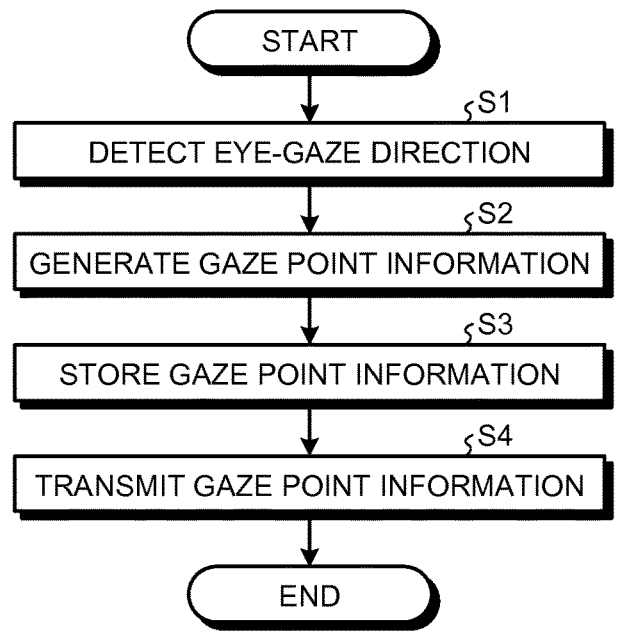
FIG. 16 is a flowchart illustrating an operation example of the PC terminal that the subject uses.

The following describes an operation example of each of the PC terminals 100 with reference to FIG. 16. FIG. 16 is a flowchart illustrating an operation example of the PC terminal 100. As illustrated in FIG. 16, the detector 101 detects an eye-gaze direction of User A (Step S1). The gaze point information generator 102 generates the gaze point information on the basis of the eye-gaze direction detected at Step S1 (Step S2), and causes the gaze point information storage unit 103 to store therein the generated gaze point information (Step S3). The gaze point information transmitter 104 transmits the gaze point information (the latest gaze point information) stored in the gaze point information storage unit 103 at Step S3 to the PC terminal 200 (Step S4).

Figure 17:
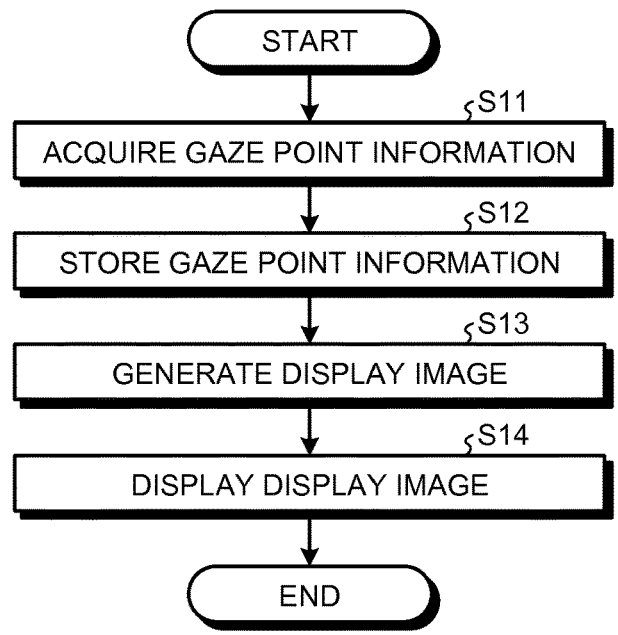
FIG. 17 is a flowchart illustrating an operation example of the PC terminal that the doctor uses.

The following describes an operation example of the PC terminal 200 when the gaze point information is acquired from the PC terminal 100 with reference to FIG. 17. FIG. 17 is a flowchart illustrating an operation example of the PC terminal 200 in this case. As illustrated in FIG. 17, the gaze point information acquiring unit 201 acquires the gaze point information transmitted from the PC terminal 100 (gaze point information transmitter 104) (Step S11), and causes the gaze point information storage unit 202 to store therein the acquired gaze point information (Step S12). The generator 207 generates a display image including, on medical checkup data displayed on the PC terminal 200, a gaze point marker displayed at a position corresponding to the gaze point information (the latest gaze point information) stored in the gaze point information storage unit 202 at Step S12 out of the medical checkup data (Step S13). The display controller 208 controls the display image generated at Step S13 to be displayed on the display unit 233 (Step S14).

Figure 18:
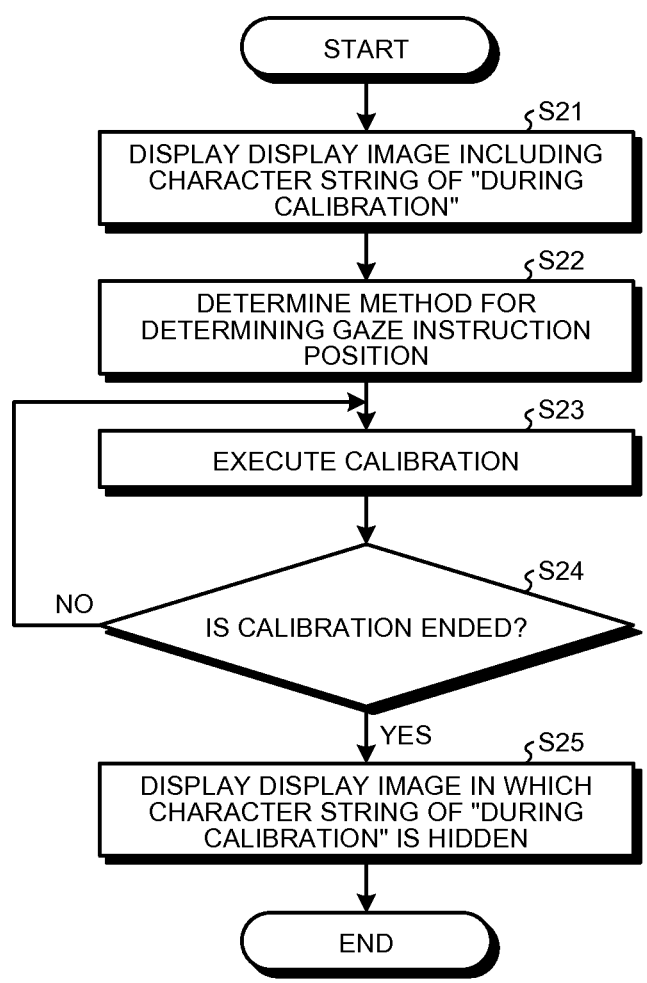
FIG. 18 is a flowchart illustrating an operation example of the PC terminal that the doctor uses.

The following describes an operation example of the PC terminal 200 when calibration is executed with reference to FIG. 18. FIG. 18 is a flowchart illustrating an operation example of the PC terminal 200 when calibration is executed. In this example, when receiving an instruction for starting calibration from User B, the determining unit 203 instructs the generator 207 and the display controller 208 to display a character string of "during calibration". The generator 207 receiving this instruction generates a display image including, on medical checkup data displayed on the PC terminal 200, a gaze point marker displayed at a position corresponding to the latest gaze point information out of the medical checkup data and the character string of "during calibration", and the display controller 208 controls the generated display image to be displayed on the display unit 233 (Step S21).

Subsequently, the determining unit 203 determines a mode for determining a gaze instruction position in accordance with an instruction for selecting any one of the first mode and the second mode from User B (Step S22), and executes calibration (Step S23). Specifically, a series of processing illustrated in FIG. 19 is repeatedly executed.

Figure 19:
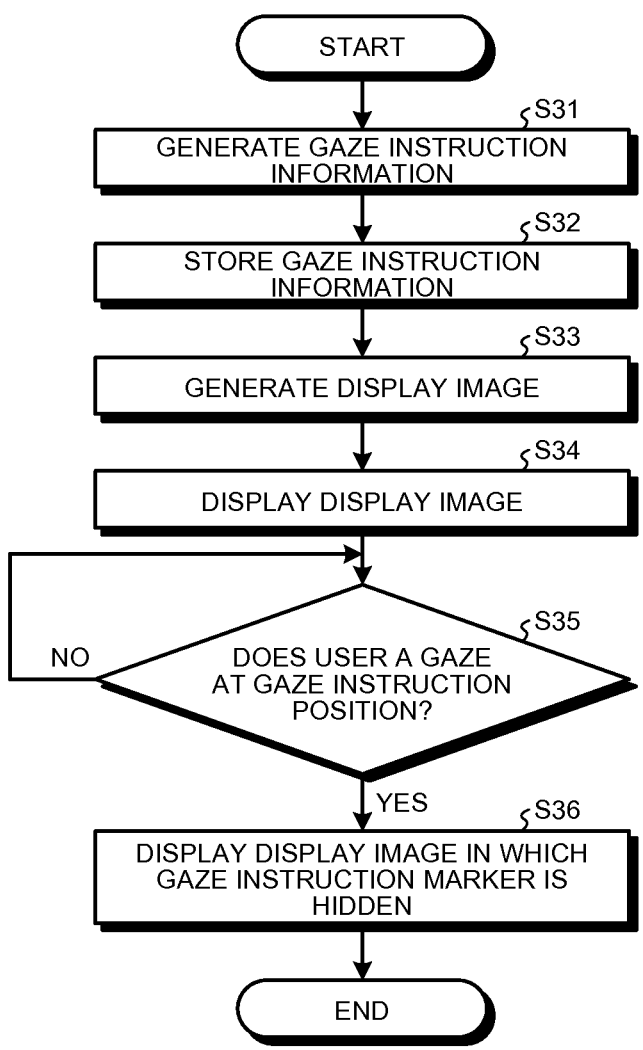
FIG. 19 is a flowchart illustrating an operation example of the PC terminal that the doctor uses.

FIG. 19 is a flowchart illustrating an operation example of the PC terminal 200 from when one gaze instruction position is determined until when User A is determined to gaze at the gaze instruction position. The following describes specific contents. As illustrated in FIG. 19, the determining unit 203 determines a gaze instruction position with a method corresponding to a mode determined at Step S22 in FIG. 18, and generates gaze instruction information indicating the determined gaze instruction position (Step S31). The method for determining a gaze instruction position is as described above. The determining unit 203 causes the gaze instruction information storage unit 204 to store therein the gaze instruction information determined at Step S31 (Step S32).

Subsequently, the generator 207 generates a display image including, on medical checkup data displayed on the PC terminal 200, a gaze point marker displayed at a position corresponding to the latest gaze point information out of the medical checkup data, a gaze instruction marker displayed at a gaze instruction position determined at Step S31 out of the medical checkup data, and a character string of "during calibration" (Step S33). The display controller 208 controls the display image generated at Step S33 to be displayed on the display unit 233 (Step S34). The determining unit 210 determines whether User A in the base A gazes at a gaze instruction position (Step S35). When determining that User A gazes at a gaze instruction position (Yes at Step S35), the determining unit 210 notifies the determining unit 203 of the determination. The determining unit 203 receiving this notification instructs the generator 207 and the display controller 208 to hide the gaze instruction marker. The generator 207 receiving this instruction generates a display image in which the gaze instruction marker is hidden (display image including, on medical checkup data displayed on the PC terminal 200, a gaze point marker displayed at a position corresponding to the latest gaze point information out of the medical checkup data and a character string of "during calibration"), and the display controller 208 controls the generated display image to be displayed on the display unit 233 (Step S36). The above description is processing contents of the flowchart illustrated in FIG. 19.

Referring back to FIG. 18, the description will be made. At Step S24 after Step S23, the calibration end determining unit 211 determines whether calibration is ended (Step S24). The method for determining the end is as described above. If the calibration is determined not to be ended (No at Step S24), the processing at Step S23 is repeated. If the calibration is determined to be ended (Yes at Step S24), the calibration end determining unit 211 notifies the determining unit 203 of the determination. The determining unit 203 receiving this notification instructs the generator 207 and the display controller 208 to hide a character string of "during calibration". The generator 207 receiving this instruction generates a display image in which the character string of "during calibration" is hidden (display image including, on medical checkup data displayed on the PC terminal 200, a gaze point marker displayed at a position corresponding to the latest gaze point information out of the medical checkup data), and the display controller 208 controls the generated display image to be displayed on the display unit 233 (Step S25). The PC terminal 200 can determine a corresponding relation between an eye-gaze direction of User A and a gaze position of User A on the basis of a plurality of data obtained by the calibration (data where an eye-gaze direction of User A is associated with a gaze instruction position).

As described above, in the embodiment, a display image including, on medical checkup data commonly displayed on the PC terminals 100 and the PC terminal 200 that are disposed in different bases, a gaze point marker displayed at a position at which User A using each of the PC terminals 100 disposed in the base A gazes on the medical checkup data and a gaze instruction marker disposed at a gaze instruction position at which User A is made to gaze on the medical checkup data is displayed on the PC terminal 200. In this manner, User B that uses the PC terminal 200 disposed in the base C views the display image and gives a gaze instruction to User A so as to perform calibration. In the embodiment, a gaze image such as a marker and the like for making User A gaze at is not necessarily displayed on the PC terminal 100 that User A uses in execution of calibration so that the calibration is executed without making User A as a calibration target conscious of the execution of the calibration. It is preferable not to give unnecessary psychological stress to the opposite side especially in mental healthcare, and the embodiment specially has an effective effect.

First Modification

Figure 20:
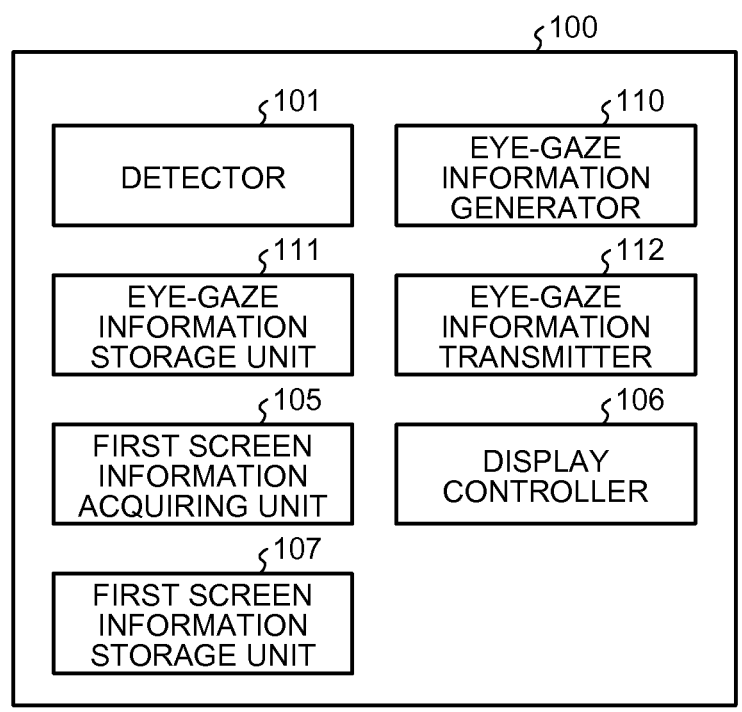
FIG. 20 is a view illustrating an example of the functional configuration of the PC terminal that the subject uses according to a first modification.

In the embodiment, the PC terminals 100 generate gaze point information, but this is not limiting and the PC terminal 200 may generate gaze point information. FIG. 20 is a view illustrating an example of the functional configuration of the PC terminal 100 according to a first modification. As illustrated in FIG. 20, the PC terminal 100 includes the detector 101, an eye-gaze information generator 110, an eye-gaze information storage unit 111, an eye-gaze information transmitter 112, the first screen information acquiring unit 105, the display controller 106, and the first screen information storage unit 107. Components other than the eye-gaze information generator 110, the eye-gaze information storage unit 111, and the eye-gaze information transmitter 112 are the same as those of the embodiment, and detailed explanation is omitted.

The eye-gaze information generator 110 generates eye-gaze information including at least an eye-gaze direction (eye-gaze direction of User A) detected by the detector 101. Eye-gaze information may be information necessary for generating gaze point information. The eye-gaze information storage unit 111 stores therein the eye-gaze information. Whenever the eye-gaze information generator 110 generates eye-gaze information, the eye-gaze information transmitter 112 transmits the eye-gaze information (the latest eye-gaze information stored in the eye-gaze information storage unit 111) to the PC terminal 200.

Figure 21:
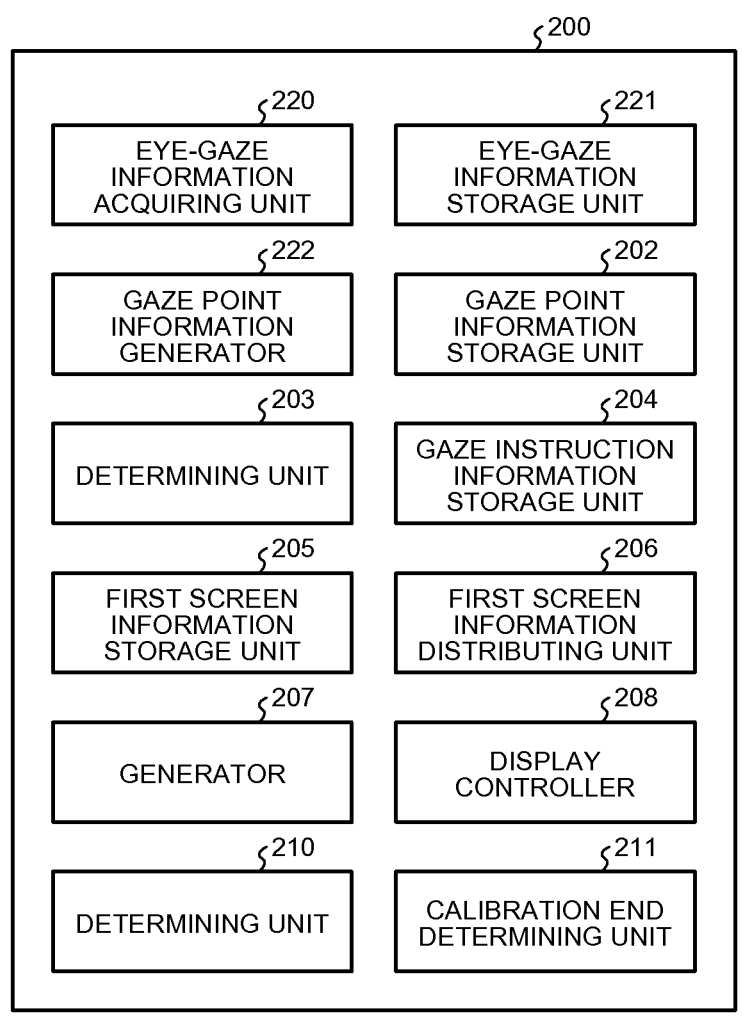
FIG. 21 is a view illustrating an example of the functional configuration of the PC terminal that the doctor uses according to the first modification.

FIG. 21 is a view illustrating an example of the functional configuration of the PC terminal 200 according to the first modification. As illustrated in FIG. 21, the PC terminal 200 includes an eye-gaze information acquiring unit 220, an eye-gaze information storage unit 221, a gaze point information generator 222, the gaze point information storage unit 202, the determining unit 203, the gaze instruction information storage unit 204, the first screen information storage unit 205, the first screen information distributing unit 206, the generator 207, the display controller 208, the determining unit 210, and the calibration end determining unit 211. Components other than the eye-gaze information acquiring unit 220, the eye-gaze information storage unit 221, and the gaze point information generator 222 are the same as those of the embodiment, and detailed explanation is omitted.

The eye-gaze information acquiring unit 220 acquires eye-gaze information from the PC terminal 100. The eye-gaze information storage unit 221 stores therein the eye-gaze information acquired by the eye-gaze information acquiring unit 220. Whenever the eye-gaze information acquiring unit 220 acquires eye-gaze information, the gaze point information generator 222 generates gaze point information on the basis of the acquired eye-gaze information (the latest eye-gaze information stored in the eye-gaze information storage unit 221), and causes the gaze point information storage unit 202 to store therein the generated gaze point information.

Figure 22:
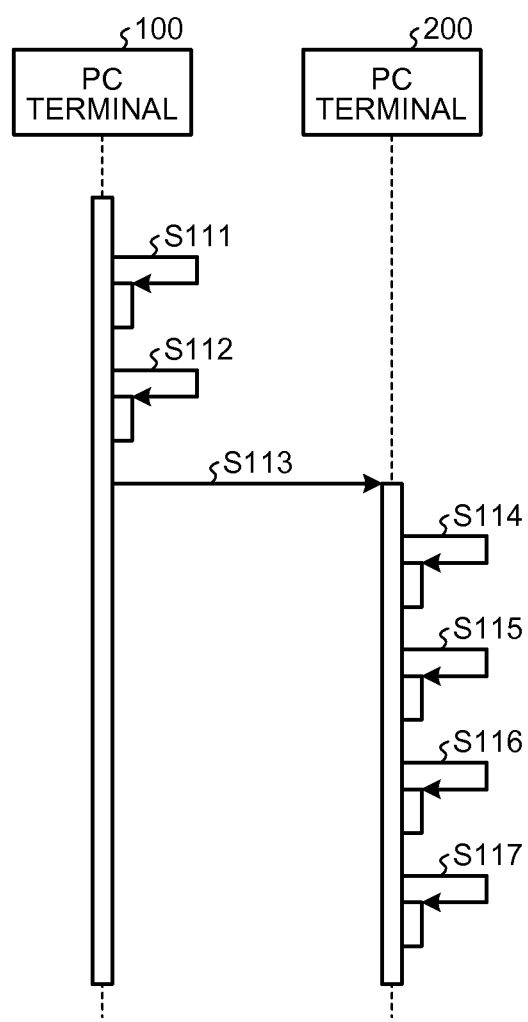
FIG. 22 is a sequence diagram illustrating an example of an operation procedure of the information processing system according to the first modification.

FIG. 22 is a sequence diagram illustrating an example of an operation procedure of the information processing system 1 according to the first modification. It is assumed that medical checkup data as the first screen information is displayed on the PC terminal 100 (display unit 123) in the base A and the PC terminal 200 (display unit 233) in the base C.

The eye-gaze information generator 110 generates eye-gaze information including at least an eye-gaze direction (eye-gaze direction of User A) detected by the detector 101 (Step S111). The eye-gaze information storage unit 111 stores therein the eye-gaze information (Step S112). Whenever the eye-gaze information generator 110 generates eye-gaze information, the eye-gaze information transmitter 112 transmits the eye-gaze information (the latest eye-gaze information stored in the eye-gaze information storage unit 111) to the PC terminal 200 (Step S113). The eye-gaze information acquiring unit 220 acquires eye-gaze information from the PC terminal 100 (Step S114). The eye-gaze information storage unit 221 stores therein the eye-gaze information acquired by the eye-gaze information acquiring unit 220 (Step S115). Whenever the eye-gaze information acquiring unit 220 acquires eye-gaze information, the gaze point information generator 222 generates gaze point information on the basis of the acquired eye-gaze information (the latest eye-gaze information stored in the eye-gaze information storage unit 221) (Step S116), and causes the gaze point information storage unit 202 to store therein the generated gaze point information (Step S117).

In this manner, the PC terminal 100 does not necessarily generate gaze point information according to the first modification, thereby reducing a load of processing in the PC terminal 100. As compared with a second modification, which will be described later, the PC terminal 100 transmits eye-gaze information and transmits no image data, thereby reducing an amount of data transmitted from the PC terminal 100 to the PC terminal 200.

In the first modification, it can be considered that the PC terminal 100 corresponds to an "external apparatus" in claims and the PC terminal 200 corresponds to an "information processing apparatus" in claims. In short, an information processing apparatus to which the present invention is applied is an information processing apparatus communicable with the external apparatus, and may have at least a function corresponding to the eye-gaze information acquiring unit 220, a function corresponding to the gaze point information generator 222, and a function corresponding to the display controller 208.

Second Modification

Figure 23:
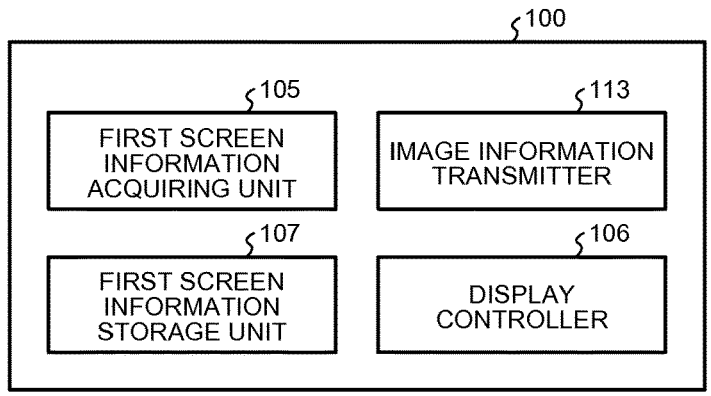
FIG. 23 is a view illustrating an example of the functional configuration of the PC terminal that the subject uses according to a second modification.

In the first modification, the PC terminal 100 generates eye-gaze information, but this is not limiting. The PC terminal 100 may transmit image information including an eye of User A and the PC terminal 200 may calculate eye-gaze information including at least an eye-gaze direction (eye-gaze direction of User A) so as to generate gaze point information. FIG. 23 is a view illustrating an example of the functional configuration of the PC terminal 100 according to the second modification. As illustrated in FIG. 23, the PC terminal 100 includes the first screen information acquiring unit 105, the display controller 106, the first screen information storage unit 107, and an image information transmitter 113. Components other than the image information transmitter 113 are the same as those of the embodiment and the first modification, and detailed explanation is omitted.

The image information transmitter 113 transmits image information including an eye of User A input from the infrared camera in the eye-gaze sensor 130 to the PC terminal 200 in a cycle.

Figure 24:
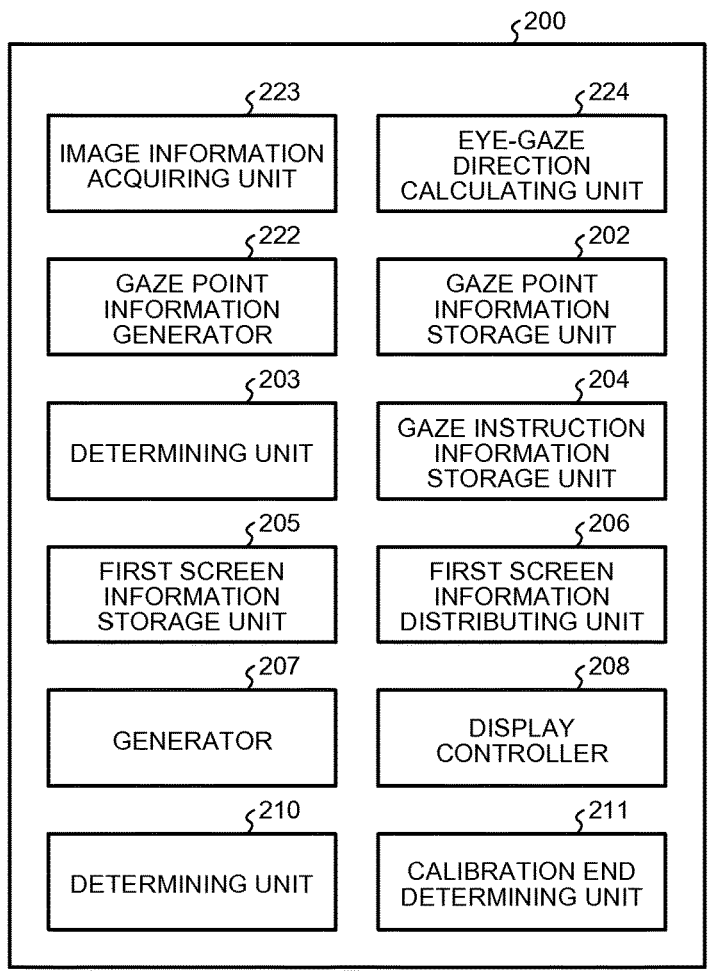
FIG. 24 is a view illustrating an example of the functional configuration of the PC terminal that the doctor uses according to the second modification.

FIG. 24 is a view illustrating an example of the functional configuration of the PC terminal 200 according to the second modification. As illustrated in FIG. 24, the PC terminal 200 includes an image information acquiring unit 223, an eye-gaze direction calculating unit 224, the gaze point information generator 222, the gaze point information storage unit 202, the determining unit 203, the gaze instruction information storage unit 204, the first screen information storage unit 205, the first screen information distributing unit 206, the generator 207, the display controller 208, the determining unit 210, and the calibration end determining unit 211. Components other than the image information acquiring unit 223 and the eye-gaze direction calculating unit 224 are the same as those of the embodiment and the first modification, and detailed explanation is omitted.

The image information acquiring unit 223 acquires image information including an eye of User A from the PC terminal 100 in a cycle.

The eye-gaze direction calculating unit 224 calculates an eye-gaze direction of User A from image information including an eye of User A using, for example, the corneal reflection method described above. Whenever the eye-gaze direction calculating unit 224 calculates an eye-gaze direction of User A, the eye-gaze direction calculating unit 224 transfers the calculated eye-gaze direction (eye-gaze information) to the gaze point information generator 222.

Figure 25:
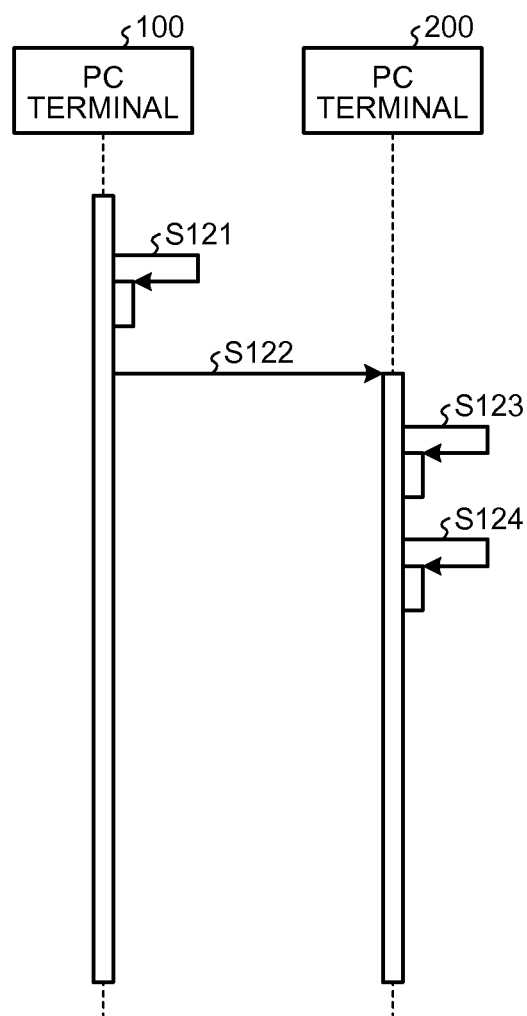
FIG. 25 is a sequence diagram illustrating an example of an operation procedure of the information processing system according to the second modification.

FIG. 25 is a sequence diagram illustrating an example of an operation procedure of the information processing system 1 according to the second modification. It is assumed that medical checkup data serving as the first screen information is displayed on the PC terminal 100 (display unit 123) in the base A and the PC terminal 200 (display unit 233) in the base C.

The PC terminal 100 acquires an input image input from the infrared camera in the eye-gaze sensor 130 (Step S121), and transmits image information to the PC terminal 200 for each cycle of the input image (Step S122). An eye-gaze direction of User A is calculated from the image information including an eye of User A that is acquired in a cycle by the image information acquiring unit 223 in the PC terminal 200 (Step S123). Whenever the eye-gaze direction calculating unit 224 calculates an eye-gaze direction of User A, the gaze point information generator 222 generates gaze point information on the basis of the calculated eye-gaze direction (the latest eye-gaze information) (Step S124). The operation after the gaze point information storage unit 202 is the same as that of the embodiment and the first modification.

In this manner, the PC terminal 100 only transmits image information including an eye of User A to the PC terminal 200, and the PC terminal 100 does not necessarily generate gaze point information and eye-gaze information according to the second modification. In other words, a dedicated application to be operated in the PC terminal 100 is not necessarily developed, and therefore development costs can be reduced.

Third Modification

Figure 26:
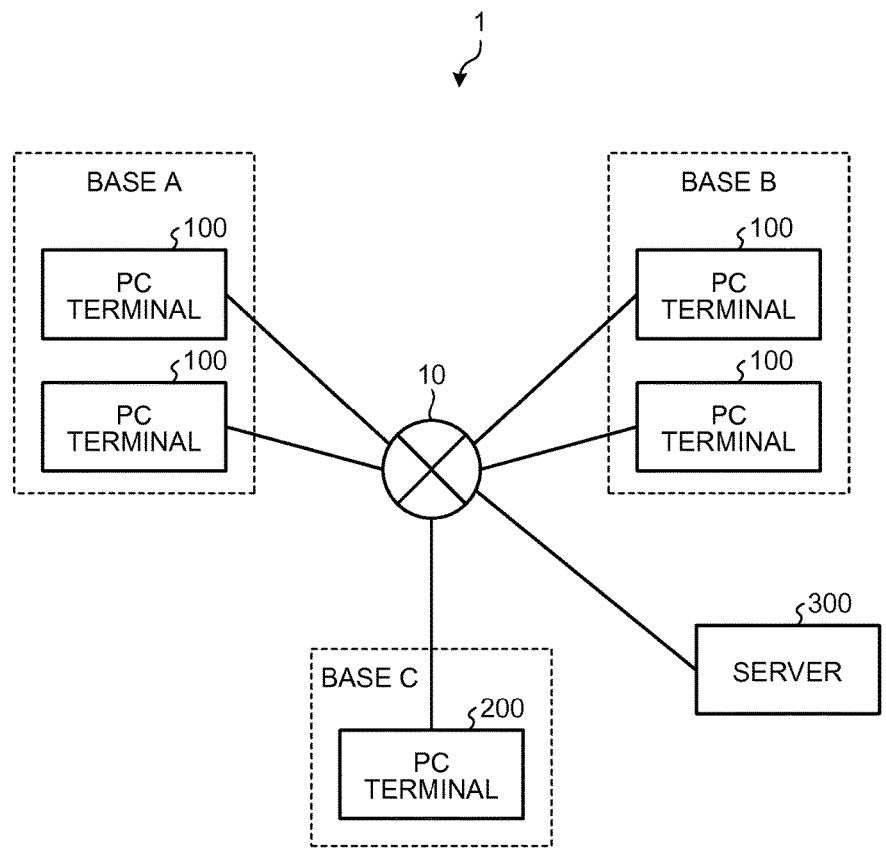
FIG. 26 is a view illustrating an example of the configuration of the information processing system according to a third modification.

FIG. 26 is a view illustrating an example of the configuration of the information processing system according to a third modification. As illustrated in FIG. 26, the information processing system 1 may further include a server 300 connected to the PC terminals 100 and the PC terminal 200 via the network 10. In other words, the third modification illustrates a configuration where the server 300 has a function of the PC terminal 200 that is described in the second modification. In the information processing system 1, each of the PC terminals 100 transmits image information including an eye of User A to the server 300 and has a function of displaying first screen information distributed from the server 300, the PC terminal 200 has a function of displaying combined screen information distributed from the server 300, and the server 300 has other functions of the information processing system 1.

Figure 27:
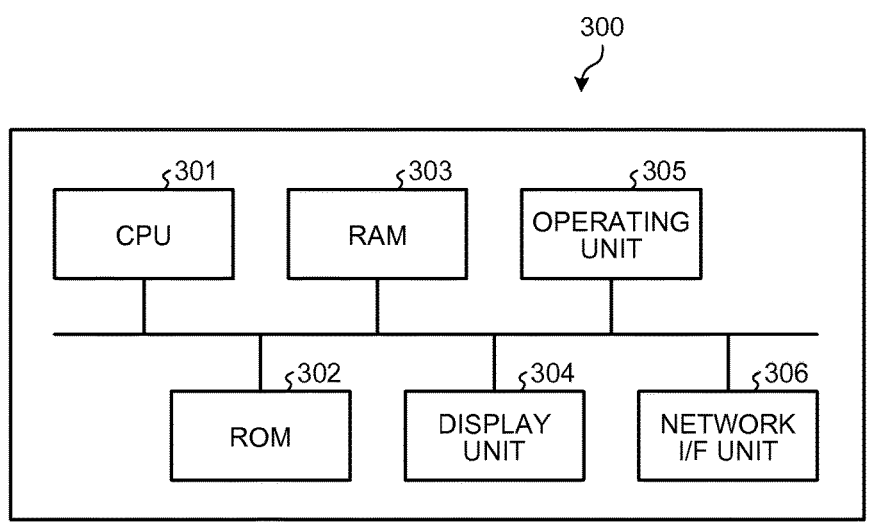
FIG. 27 is a view illustrating an example of the hardware configuration of a server according to the third modification.

FIG. 27 is a view illustrating an example of the hardware configuration of the server 300. As illustrated in FIG. 27, the server 300 includes a CPU 301, a ROM 302, a RAM 303, a display unit 304, an operating unit 305, and a network I/F unit 306. The CPU 301 integrally controls operation of the server 300. The ROM 302 is nonvolatile memory that stores therein various kinds of data such as a computer program. The RAM 303 is volatile memory that functions as a work area (task area) of the CPU 301. The display unit 304 is a device that displays various kinds of information, and may be formed by, for example, a liquid crystal display. The operating unit 305 is a device used for various kinds of operation, and may be formed by, for example, a keyboard, a mouse and the like. The network I/F unit 306 is an interface for connecting with the network 10.

For example, the server 300 has a function of distributing first screen information to each of the PC terminals 100 and distributing a display image formed by superimposing (combining) a second image displayed at a position indicated by gaze point information and a third image displayed at a gaze instruction position at which a first user is made to gaze on the first screen information as combined screen information to the PC terminal 200. In other words, the combined screen information is a display image including a gaze point marker, a gaze instruction marker, and a character string of "during calibration" on medical checkup data (In the example of FIG. 12, a display image formed by superimposing (combining) a gaze point marker, a gaze instruction marker, and a character string of "during calibration" on medical checkup data) as described with reference to FIG. 12.

Figure 28:
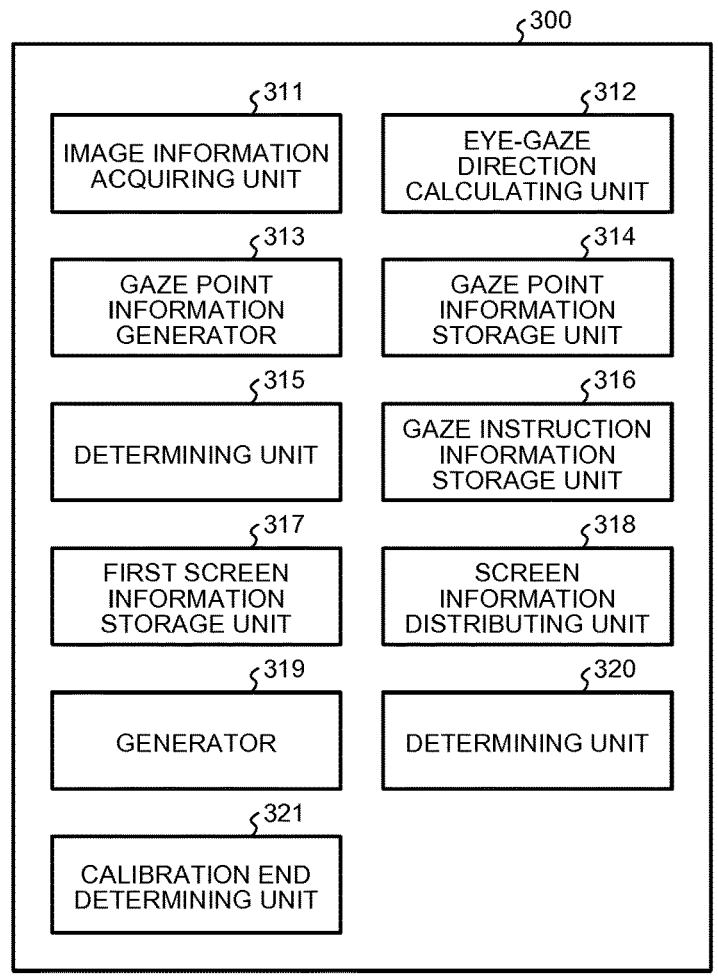
FIG. 28 is a view illustrating an example of the functional configuration of the server according to the third modification.

FIG. 28 is a view illustrating an example of the functional configuration of the server 300 according to the third modification. As illustrated in FIG. 28, the server 300 includes an image information acquiring unit 311, an eye-gaze direction calculating unit 312, a gaze point information generator 313, a gaze point information storage unit 314, a determining unit 315, a gaze instruction information storage unit 316, a first screen information storage unit 317, a screen information distributing unit 318, a generator 319, a determining unit 320, and a calibration end determining unit 321. Components other than the screen information distributing unit 318 are the same as those of the embodiment and the second modification, and detailed explanation is omitted. In other words, the function of the image information acquiring unit 311 is the same as that of the image information acquiring unit 223, the function of the eye-gaze direction calculating unit 312 is the same as that of the eye-gaze direction calculating unit 224, the function of the gaze point information generator 313 is the same as that of the gaze point information generator 222, the function of the gaze point information storage unit 314 is the same as that of the gaze point information storage unit 202, the function of the determining unit 315 is the same as that of the determining unit 203, the function of the gaze instruction information storage unit 316 is the same as that of the gaze instruction information storage unit 204, the function of the first screen information storage unit 317 is the same as that of the first screen information storage unit 205, the function of the generator 319 is the same as that of the generator 207, the function of the determining unit 320 is the same as that of the determining unit 210, and the function of the calibration end determining unit 321 is the same as that of the calibration end determining unit 211.

The screen information distributing unit 318 distributes first screen information stored in the first screen information storage unit 317 to the PC terminals 100 and distributes a display image formed by superimposing (combining) a second image displayed at a position indicated by gaze point information and a third image displayed at a gaze instruction position at which a first user is made to gaze on the first screen information as combined screen information to the PC terminal 200.

Figure 29:
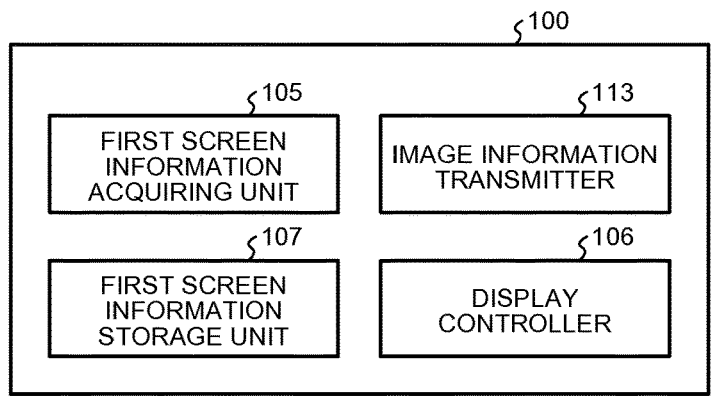
FIG. 29 is a view illustrating an example of the functional configuration of the PC terminal that the subject uses according to the third modification.

FIG. 29 is a view illustrating an example of the functional configuration of each of the PC terminals 100 according to the third modification. As illustrated in FIG. 29, the PC terminal 100 includes the first screen information acquiring unit 105, the display controller 106, the first screen information storage unit 107, and the image information transmitter 113. Components of each unit are the same as those of the embodiment and the second modification, and detailed explanation is omitted.

Figure 30:
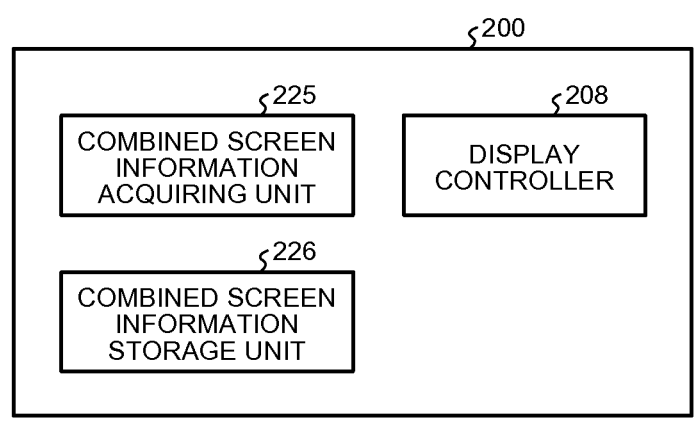
FIG. 30 is a view illustrating an example of the functional configuration of the PC terminal that the doctor uses according to the third modification.

FIG. 30 is a view illustrating an example of the functional configuration of the PC terminal 200 according to the third modification. As illustrated in FIG. 30, the PC terminal 200 includes a combined screen information acquiring unit 225, a combined screen information storage unit 226, and the display controller 208.

The combined screen information acquiring unit 225 acquires combined screen information distributed from the server 300. The combined screen information is a display image formed by superimposing (combining) a second image displayed at a position indicated by gaze point information and a third image displayed at a gaze instruction position at which a first user is made to gaze on the first screen information.

The combined screen information storage unit 226 stores therein combined screen information acquired by the combined screen information acquiring unit 225. The combined screen information storage unit 226 stores therein, for example, combined screen information serving as a display image that is formed by superimposing (combining) a second image displayed at a position indicated by gaze point information and a third image displayed at a gaze instruction position at which a first user is made to gaze on the first screen information.

The display controller 208 controls the combined display image to be displayed on the display unit 233 on the basis of the combined screen information acquired by the combined screen information acquiring unit 225.

In this manner, each of the PC terminals 100 only transmits image information including an eye of User A to the server 300 and the PC terminal 200 only displays combined screen information distributed from the server 300 according to the third modification. The server 300 performs other processing, and a dedicated application to be operated in the PC terminals 100 and the PC terminal 200 is not necessarily developed, and therefore development costs can be reduced.

The above-mentioned case is not limiting and the server 300 can be equipped with a part of the functions that the PC terminals 100 have or a part of the functions that the PC terminal 200 has.

Computer Program

The computer program executed by the information processing system 1 in the embodiment is a file in a computer-installable format or in an executable format, and may be recorded and provided in computer-readable recording media such as compact disc read only memory (CD-ROM), a flexible disk (FD), compact disc recordable (CD-R), a digital versatile disc (DVD), universal serial bus (USB) and the like. The computer program may be provided or distributed via a network such as the Internet. Various kinds of computer programs may be preliminarily incorporated in nonvolatile recording media such as a ROM so as to be provided.

According to the present invention, calibration can be executed without making a user as a calibration target conscious of the execution of calibration.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An information processing system comprising:
a first information processing apparatus including a first display, a sensor and a first processor, the first processor configured to,
  detect an eye-gaze direction of a first user that uses the first information processing apparatus based on data from the sensor, and
  generate, basis on the eye-gaze direction, gaze point information indicating an actual gaze position at which the first user actually gazes within coordinates of a first copy of first screen information displayed on the first display associated with the first information processing apparatus; and
a second information processing apparatus communicable with the first information processing apparatus, the second information processing apparatus including a second display and a second processor, the second processor configured to calibrate a correspondence relation between the eye-gaze direction of the first user and the actual gaze position of the first user by,
  determining a position at which the first user is expected to gaze within the coordinates of the first screen information displayed on the first display as a gaze instruction position,
  superimposing both the actual gaze position and the gaze instruction position of the first user on a second copy of the first screen information to generate a superimposed screen information, and
  controlling, the second display, to display the superimposed screen information such that the first screen information is commonly displayed with the first copy thereof being displayed on the first display and the second copy including the superimposed screen information being displayed on the second display associated with a second user.

2. The information processing system according to claim 1, wherein the second processor is configured to determine whether the first user gazes at the gaze instruction position, based on a position relation between the actual gaze position and the gaze instruction position.

3. The information processing system according to claim 2, wherein the second processor is configured to determine that the first user gazes at the gaze instruction position when a difference between the actual gaze position and the gaze instruction position is less than or equal to a threshold.

4. The information processing system according to claim 3, wherein the second processor is configured to,
  iteratively determine whether the difference between the actual gaze position and the gaze instruction position is less than or equal to the threshold, and
  determine that the first user gazes at the gaze instruction position, if a number of times that the difference is less than or equal to the threshold is at least an iteration threshold.

5. The information processing system according to claim 1, wherein
  the first screen information includes a plurality of characteristic areas capable of being gazed at by the first user, and
  the second processor is configured to determine that the first user gazes at the gaze instruction position, when the characteristic area corresponding to the actual gaze position is identical to the characteristic area corresponding to the gaze instruction position.

6. The information processing system according to claim 5, wherein the second processor is configured to,
  iteratively determine whether the characteristic area corresponding to the actual gaze position is identical to the characteristic area corresponding to the gaze instruction position, and
  determine that the first user gazes at the gaze instruction position, if a number of times that the characteristic areas are determined to be identical is equal to or greater than an iteration threshold.

7. The information processing system according to claim 1, wherein
  the first screen information includes a plurality of characteristic areas capable of being gazed at by the first user, and
  the second processor is configured to determine, according to a rule, one of the characteristic areas to be the gaze instruction position.

8. The information processing system according to claim 7, wherein the second processor is configured to determine a new gaze instruction position, when the first user is determined to gaze at the characteristic area different from the characteristic area corresponding to the gaze instruction position.

9. The information processing system according to claim 7, wherein the second processor is configured to determine a new gaze instruction position, when the first user is not determined to gaze at the gaze instruction position in a certain period from when the gaze instruction position is determined.

10. The information processing system according to claim 7, wherein the characteristic area is an area corresponding to one of a plurality of items included in a table structure.

11. The information processing system according to claim 1, wherein
  the first screen information includes a plurality of characteristic areas capable of being gazed at by the first user, and
  the second processor is configured to determine one of the characteristic areas to be the gaze instruction position in accordance with a selection instruction by the second user that uses the second information processing apparatus.

12. The information processing system according to claim 11, wherein the second processor is configured to, divide the first screen information into a plurality of selection ranges each including one or more of the characteristic areas, and set at least one selection range out of the selection ranges as the selection range capable of receiving the selection instruction by the second user.

13. The information processing system of claim 1, wherein subsequent to calibrating the correspondence relation between the eye-gaze direction of the first user and the actual gaze position of the first user, the information processing system is configured to operate in response to the eye-gaze direction of the first user based on the correspondence relation.

14. The information processing system according to claim 1, wherein the second processor is configured to control the second display to hide the gaze instruction marker in the superimposed screen information in response to the second processor determining that the first user is gazing at the gaze instruction position.

15. The information processing system according to claim 1, wherein the second processor is configured to determine a new characteristic area different from a prior characteristic area corresponding to the gaze instruction position determined to have been gazed at by first user, as a new gaze instruction position.

16. The information processing system according to claim 1, wherein the second processor is configured to determine a new gaze instruction position in response to the second processor determining that the first user gazes at the gaze instruction position.

17. The information processing system according to claim 1, wherein the second processor is configured to receive instruction for selecting an operating mode from among a first mode and a second mode, the first mode being a mode in which the second processor automatically determines a gaze instruction position, and the second mode being a mode in which the gaze instruction position is determined manually.

18. An information processing method performed by an information processing apparatus communicable with an external apparatus, the external apparatus including a first display and the information processing apparatus including a second display, the method comprising:

calibrating a correspondence relation between an eye-gaze direction of a first user associated with the external apparatus and an actual gaze position of eyes of the first user by, determining a position at which the first user is expected to gaze within coordinates of a first copy of first screen information displayed on the first display as a gaze instruction position, superimposing both the actual gaze position and the gaze instruction position of the first user on a second copy of the first screen information to generate a superimposed screen information, and controlling, the second display, to display the superimposed screen information such that the first screen information is commonly displayed with the first copy thereof being displayed on the first display and the second copy including the superimposed screen information being displayed on the second display associated with a second user.

19. An information processing method performed by an information processing apparatus communicable with an external apparatus, the external apparatus including a first display and the information processing apparatus including a second display, the method comprising:

calibrating a correspondence relation between an eye-gaze direction of a first user associated with the external apparatus and an actual gaze position of eyes of the first user by, acquiring eye-gaze information including at least the eye-gaze direction from the external apparatus including a detector that detects the eye-gaze direction of the first user that uses the external apparatus, generating, based on the eye-gaze information, gaze point information indicating an actual gaze position at which the first user gazes within coordinates of a first copy of first screen information displayed on the first display associated with the external apparatus, and determining a position at which the first user is expected to gaze within the coordinates of the first screen information displayed on the first display as a gaze instruction position, superimposing both the actual gaze position and the gaze instruction position of the first user on a second copy of the first screen information to generate a superimposed screen information, and controlling, the second display, to display the superimposed screen information such that the first screen information is commonly displayed with the first copy thereof being displayed on the first display and the second copy including the superimposed screen information being displayed on the second display associated with a second user.

* * * * *